US012685813B2

(12) United States Patent
Lee et al.

(10) Patent No.: US 12,685,813 B2
(45) Date of Patent: Jul. 21, 2026

(54) FIELD-CHARGEABLE TRANSCUTANEOUS DRUG DELIVERY SYSTEM

(71) Applicant: Zyno Medical, LLC, Natick, MA (US)

(72) Inventors: Chao Young Lee, Weston, MA (US);
Mei Zhang, Sharon, MA (US);
Zhenhua Mao, Andover, MA (US)

(73) Assignee: Zyno Medical LLC, Natick, MA (US)

(*) Notice: Subject to any disclaimer, the term of this
patent is extended or adjusted under 35
U.S.C. 154(b) by 1002 days.

(21) Appl. No.: 17/894,326

(22) Filed: Aug. 24, 2022

(65) Prior Publication Data

US 2023/0083092 A1 Mar. 16, 2023

Related U.S. Application Data

(60) Provisional application No. 63/236,292, filed on Aug.
24, 2021.

(51) Int. Cl.
*A61M 5/142* (2006.01)
*A61M 5/32* (2006.01)
*A61M 5/34* (2006.01)

(52) U.S. Cl.
CPC .... *A61M 5/14248* (2013.01); *A61M 5/14216*
(2013.01); *A61M 5/3286* (2013.01); *A61M
5/3287* (2013.01); *A61M 5/34* (2013.01);
*A61M 2005/14252* (2013.01)

(58) Field of Classification Search
CPC ............ A61M 5/14216; A61M 5/3286; A61M
5/3287; A61M 5/34; A61M 5/14248;
A61M 5/178; A61M 2005/14252; A61M
2005/1585; A61M 2209/045
See application file for complete search history.

(56) References Cited

U.S. PATENT DOCUMENTS

| 5,957,891 | A | * | 9/1999 | Kriesel | ................ | A61M 31/002 |
| | | | | | | 604/890.1 |
| 7,128,727 | B2 | * | 10/2006 | Flaherty | ................. | G16H 20/17 |
| | | | | | | 604/131 |
| 7,918,825 | B2 | | 4/2011 | O'Connor et al. | | |
| 9,061,097 | B2 | * | 6/2015 | Holt | .................. | A61M 5/14248 |
| 10,130,758 | B2 | | 11/2018 | Diianni et al. | | |
| 10,438,696 | B2 | | 10/2019 | Shapley et al. | | |
| 10,569,011 | B2 | | 2/2020 | Dianni et al. | | |
| 10,777,319 | B2 | | 9/2020 | Shapley et al. | | |

(Continued)

FOREIGN PATENT DOCUMENTS

WO 2021050494 A1 3/2021

OTHER PUBLICATIONS

International Search Report and Written Opinion for Application
No. PCT/US2022/041225 dated Jan. 13, 2023 (15 pages).

(Continued)

*Primary Examiner* — James D Ponton
(74) *Attorney, Agent, or Firm* — Boyle Fredrickson, S.C

(57) ABSTRACT

An automatic needle insertion device assists patients who
may be uncomfortable with placing the needle themselves
and employs a soft outer needle inserted using a rigid stylet,
for example, a standard hypodermic needle, which is then
removed after the soft needle is placed, greatly reducing
irritation. An ambulatory pump can be filled with a variety
of drugs and different amounts of drug on demand, for
example, using a syringe prior to use.

18 Claims, 2 Drawing Sheets

(56)            References Cited

U.S. PATENT DOCUMENTS

| | | | |
|---|---|---|---|
| 2004/0092865 A1* | 5/2004 | Flaherty | A61M 5/1452 604/93.01 |
| 2007/0299398 A1 | 12/2007 | Alferness et al. | |
| 2009/0143732 A1 | 6/2009 | O'Connor et al. | |
| 2017/0043090 A1 | 2/2017 | Mueller-Pathle | |
| 2019/0015585 A1 | 1/2019 | Smith | |
| 2019/0143039 A1* | 5/2019 | Moberg | A61M 5/172 604/131 |
| 2019/0151544 A1 | 5/2019 | Stonecipher | |
| 2020/0078513 A1* | 3/2020 | Wei | A61M 5/16804 |

OTHER PUBLICATIONS

European Search Report and Written Opinion for Application No. 22861986.2 dated Apr. 23, 2025 (9 pages).

* cited by examiner

FIELD-CHARGEABLE TRANSCUTANEOUS DRUG DELIVERY SYSTEM

CROSS REFERENCE TO RELATED APPLICATION

This application claims the benefit of U.S. Provisional Application No. 63/236,292, filed Aug. 24, 2021, hereby incorporated by reference.

BACKGROUND OF THE INVENTION

The present invention relates to devices for the automatic delivery of drugs to a patient and, in particular, to a drug delivery device allowing field loading of drugs.

The ability to meter intravenous drug administration over a long period of time can provide better efficacy of the drug and less toxicity to a patient. For this purpose, ambulatory infusion pumps have been developed, for example, that can be carried on the patient in a harness or the like.

An improved class of ambulatory pumps may attach directly to the patient's skin and also provide for automatic needle insertion. Pumps of this kind are normally pre-charged with small quantities of the particular drug and thus present shelf-life and inventory challenges. In addition, the pump housing can be uncomfortable when attached to the patient's skin and the automatically inserted hypodermic needle can be irritated with normal daily activity.

SUMMARY OF THE INVENTION

The present invention provides an ambulatory pump that can be filled with a variety of drugs and different amounts of drug on demand, for example, using a syringe prior to use. In this way, inventoried pumps have a prolonged shelf life and greater versatility improving inventory management. An automatic needle insertion device assists patients who may be uncomfortable with placing the needle themselves and employs a soft outer needle inserted using a rigid stylet (for example, a standard hypodermic needle) which is then removed after the soft needle is placed, greatly reducing irritation.

Specifically, the present invention provides a transcutaneous drug delivery system receiving a syringe containing a liquid comprising an ambulatory pump providing a pump housing attachable to skin of a patient; a syringe coupling supported by and exposed on an exterior of the pump housing providing a leak-free connection between the syringe and the syringe coupling; and a hypodermic needle supported by the pump housing along an insertion path of the hypodermic needle into the skin of the patient and coupled to the syringe coupling to fluidly communicate with the syringe to receive the liquid.

It is thus a feature of at least one embodiment of the present invention to improve patient comfort when attaching the syringe to the automatic needle insertion device by using a lower force, twist connector.

A collar may surround the syringe coupling on an exterior of the pump housing. The collar may extend outwardly from the pump housing by at least 1 cm.

It is thus a feature of at least one embodiment of the present invention to stabilize the connection of the syringe tip to the automatic needle insertion device when, for example, the syringe plunger is being pressed by the user to expel liquid.

The syringe coupling is a Luer-Lock connector providing a one way valve. A syringe may have a Luer-Lock tip.

It is thus a feature of at least one embodiment of the present invention to prevent leakage when the syringe is removed from the automatic needle insertion device. It is also a feature of the present invention to allow the automatic needle insertion device to be compatible with standard Luer-Lock syringes.

A reservoir may fluidly communicate with the hypodermic needle to receive a liquid.

It is thus a feature of at least one embodiment of the present invention to allow for larger amounts of drug to be delivered to the patient over a longer span of time while the device is worn by the patient.

A cannula manifold may receive the hypodermic needle and comprise a soft needle receiving the hypodermic needle therein.

It is thus a feature of at least one embodiment of the present invention to allow a softer needle to remain within the patient's skin for drug delivery, reducing discomfort and irritation to the patient.

The cannula manifold may further comprise a channel communicating with the reservoir to permit movement of liquid between the cannula manifold and the reservoir.

It is thus a feature of at least one embodiment of the present invention to quickly fill the reservoir with drugs using a common manifold that can be selectively closed to divert a single flow path from the needle to the reservoir.

A first one way check valve may permit movement of liquid from the cannula manifold to the reservoir and a second one way check valve permitting movement of liquid from the reservoir to the cannula manifold.

It is thus a feature of at least one embodiment of the present invention to manage the one way, directional flow of drugs to and from the reservoir while also eliminating gases within the reservoir.

An apex of the soft needle may be pierceable by the hypodermic needle permitting passage of the hypodermic needle through the skin of the patient.

It is thus a feature of at least one embodiment of the present invention to deliver drugs from the reservoir using a common manifold that can be selectively opened to divert a single flow path from the reservoir to the needle. In this respect, the present invention prevents passage of fluid through the soft needle during a first drug filling step and allows passage of fluid through the soft needle during a second drug delivery step.

A pump may be configured to draw liquid from the reservoir. The pump may comprise a motor reciprocating a piston within a cylinder.

It is thus a feature of at least one embodiment of the present invention to use a small and discrete pump allowing the device to be worn on the patient's body so that the patient can continue their normal daily activity during drug delivery.

A first compression spring may be configured to move the hypodermic needle along the insertion path through the skin of the patient in a released state.

It is thus a feature of at least one embodiment of the present invention to rapidly insert the hypodermic needle jointly with the soft needle to reduce patient discomfort. It is also a feature of the present invention to allow the needle to be automatically deployed with less force by the user.

A second compression spring may exert a greater force than the first compression spring and may be configured to move the hypodermic needle out of the skin of the patient and out of the soft needle. A spring catch may retain the second compression spring in a compressed state until the hypodermic needle is moved along the insertion path through the skin of the patient.

It is thus a feature of at least one embodiment of the present invention to rapidly remove the hypodermic needle from the patient's skin without an intervening step requiring user manual action and in a manner which safely leaves the soft needle within the skin for drug delivery.

A needle insertion membrane may be supported by the pump housing along the insertion path through the skin of the patient allowing the hypodermic needle to pierce the membrane and reseal when the hypodermic needle is removed from the membrane.

It is thus a feature of at least one embodiment of the present invention to prevent the backflow of drugs back into the hypodermic needle or syringe after the hypodermic needle pierces the patient's skin and is no longer needed.

The present invention also provides a method of transcutaneous delivering a drug from a syringe containing a liquid comprising attaching an ambulatory pump providing a pump housing to skin of a patient, the ambulatory pump having a syringe coupling supported by and exposed on an exterior of the pump housing providing a leak-free connection between the syringe and the syringe coupling, a hypodermic needle supported by the pump housing and coupled to the syringe coupling to fluidly communicate with the syringe, and a reservoir fluidly communicating with the hypodermic needle to receive a liquid; connecting the syringe to the syringe coupling; expelling the liquid from the syringe through the hypodermic needle to fill the reservoir; piercing the skin of the patient with the hypodermic needle contemporaneously with a coextending soft needle; and retracting the hypodermic needle from the skin leaving the soft needle in the skin of the patient; and pumping liquid from the reservoir through the soft needle into the skin of the patient.

It is thus a feature of at least one embodiment of the present invention to provide a multipurpose hypodermic needle to first deliver drugs to the reservoir and then to puncture the patient's skin for transcutaneous drug delivery in a second step thus simplifying the device.

The method may further comprise piercing an apex of the soft needle with the hypodermic needle.

The present invention also provides a transcutaneous drug delivery system receiving a syringe containing a liquid comprising an ambulatory pump providing a pump housing attachable to skin of a patient; a syringe coupling supported by the pump housing providing a leak-free connection between the syringe and the syringe coupling; a hypodermic needle supported by the pump housing along an insertion path of the hypodermic needle into the skin of the patient and coupled to the syringe coupling to fluidly communicate with the syringe to receive the liquid; and a compression spring configured to move the hypodermic needle along the insertion path through the skin of the patient in a released state.

It is thus a feature of at least one embodiment of the present invention to provide quick release and quick retraction of the delivery needle along an axis into the skin without rotation of the needle into and out of the patient's skin.

Tabs may be configured to be pressed to release the compression spring to the released state.

These particular objects and advantages may apply to only some embodiments falling within the claims and thus do not define the scope of the invention.

DETAILED DESCRIPTION OF THE PREFERRED EMBODIMENT

Figures 1, 2, 3, 4, 5:
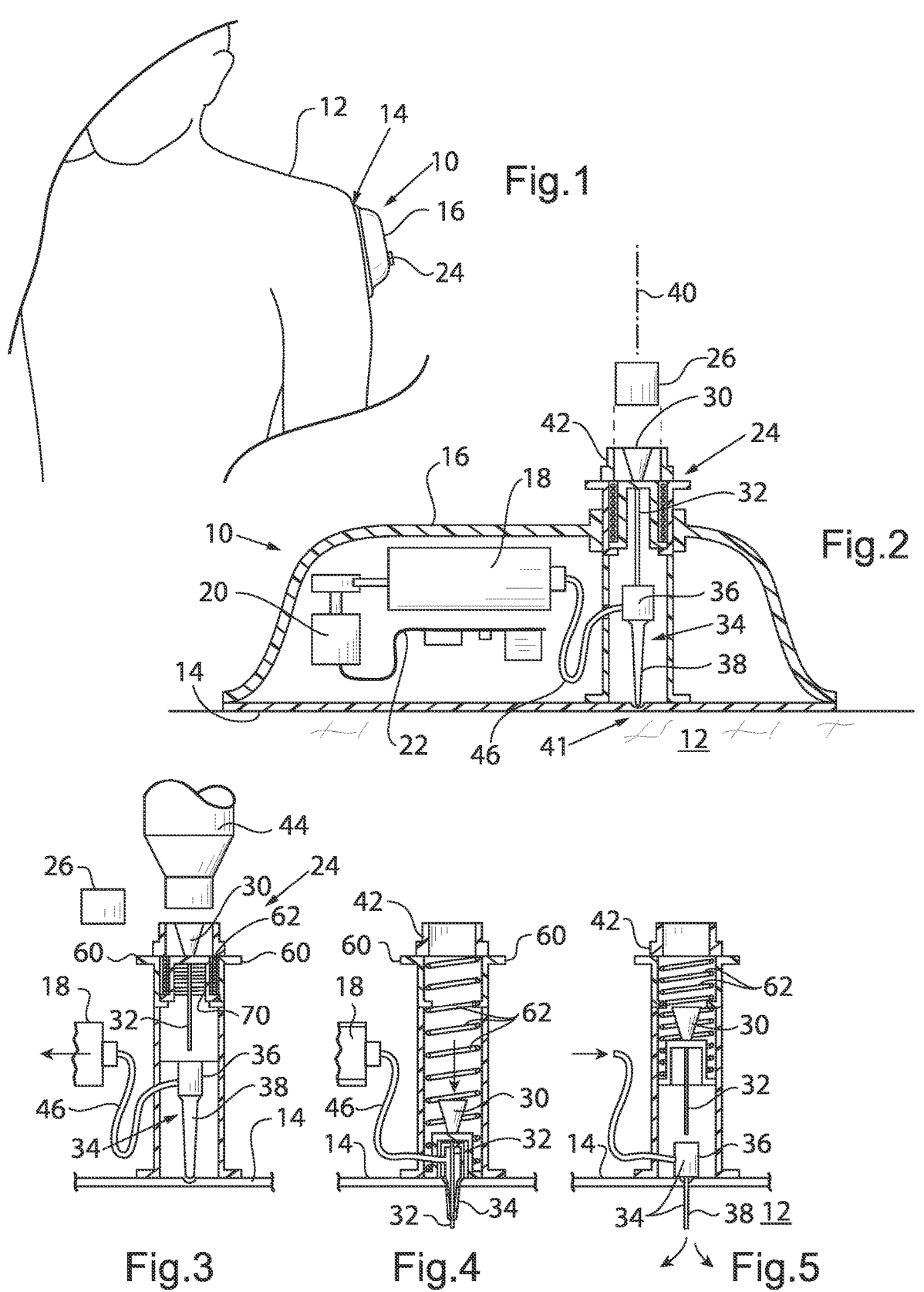
FIG. 1 is a fragmentary elevational view of a patient's shoulder showing an example ambulatory pump per the present invention adhered thereto.
FIG. 2 is a simplified cross-section of the ambulatory pump of FIG. 1 showing an internal reservoir pump and electronics together with an automatic needle insertion assembly contained in a rigid or soft housing.
FIG. 3 is a figure showing attachment of a syringe to the ambulatory pump for filling of the reservoir through an exposed smart Luer lock attached to a rigid hypodermic needle.
FIG. 4 is a figure similar to that of FIG. 3 showing deployment of the automatic needle insertion apparatus for inserting a soft cannula into the skin guided by the rigid hypodermic needle.
FIG. 5 is a figure similar to FIGS. 3 and 4 showing subsequent retraction of the needle leaving only the soft cannula in place.

Referring now to FIG. 1, an ambulatory pump 10 may attach, for example, to the skin of a patient 12, for example, on the shoulder, by means of a pressure-sensitive, adhesive-coated foot 14 forming part of a pump housing 16. In one embodiment, the pump housing 16 may be an elastomeric material such as a silicone rubber to flexibly conform to the skin and to provide improved patient comfort under clothing or with minor impacts.

Referring now to FIG. 2, the housing 16 holds a drug reservoir 18 which may have an internal pumping mechanism driven by electric pump motor 20 as will be described below. Electric pump motor 20 communicates, for example, with a flexible circuit board 22 having necessary pump-driving circuitry, batteries, and the like as is understood in the art. The flexible circuit board 22 may also provide for monitoring and control of various sensors including flow rate sensors, pressure sensors, occlusion sensors, reservoir fill sensors and the like. Example mechanisms suitable for ambulatory pumps 10 are described in US patent application publications 2016/0175519 and 2016/0058940, assigned to the assignee of the present application and hereby incorporated by reference.

The housing 16 may support a needle insertion mechanism 24 having a portion exposed from the housing 16 and presenting a removable cap 26 covering a so-called "smart" Luer lock 30 attached to a hypodermic needle 32 of conventional design. The smart Luer lock 30 operates in the manner of a standard needle Luer lock fitting but provides a one-way valve capability preventing leakage backward out of the Luer lock 30 once a syringe has been disconnected from the Luer lock 30. In some embodiments, a Luer slip as known in the art may be used in a similar manner as the Luer lock 30.

The hypodermic needle 32 associated with the Luer lock 30 may be a standard stainless steel hypodermic needle for intravenous drug administration and is oriented within the needle insertion mechanism 24 to be aligned with and to move along an axis 40 for insertion into the patient 12. Along this line of insertion, between the hypodermic needle 32 and the patient 12 is a soft cannula assembly 34 having an upper T-housing 36 positioned above a soft needle 38. The hypodermic needle 32 is sized to be received coaxially within the soft needle 38 and to be jointly inserted through the patient's skin through a thin portion 41 of the foot 14 that may be pierced by the soft needle 38 during the insertion process.

While the Luer lock 30 is exposed outside of the housing 16 it may be surrounded by a protective collar 42 sized to allow attachment of the Luer lock 30 to a standard syringe 44 as shown in FIG. 3 and which may serve to stabilize the syringe 44. The protective collar 42 may extend outwardly from the outside of the housing 16 by at least 1 cm and by at least 1.5 cm and by at least 2 cm. Generally, the needle insertion mechanism 24 provides for movement of the hypodermic needle 32 automatically downward into the cannula assembly 34 to carry the soft needle 38 and hypodermic needle 32 into the skin of the patient 12. In this respect, the relatively stiff hypodermic needle 32 provides a stylet allowing the soft needle 38, typically a relatively flexible polymer, to pierce the skin. After this piercing operation, the hypodermic needle 32 is retracted leaving only the soft needle 38 in place as will be discussed in more detail below. Movement of the T-housing 36 of the cannula assembly 34 during this insertion process is facilitated by a flexible tube 46 communicating between the T-housing 36 and the reservoir 18.

Referring now to FIG. 3, during use and as noted above, a syringe 44 may be attached to the Luer lock 30 by rotation as is understood in the art and a drug in the syringe 44 may be transferred to the reservoir 18 through tube 46 from T-housing 36.

Figures 6, 7, 8, 9, 10, 11:
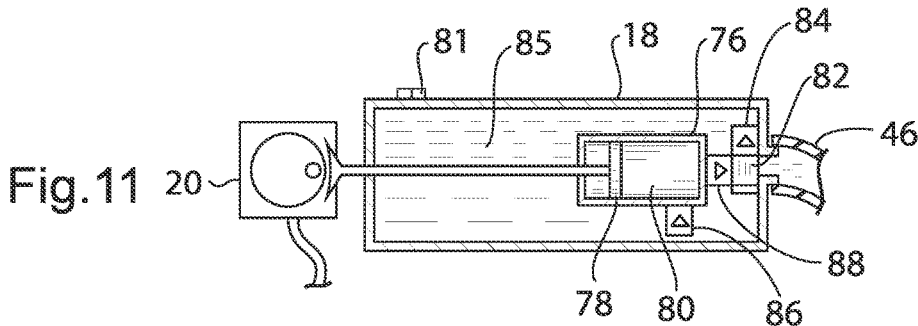
FIG. 6 is a detailed cross-sectional view of the cannula showing a self-sealing opening in a closed position.
FIG. 7 is a figure similar to FIG. 6 showing the insertion of the rigid hypodermic needle into the cannula through the self-sealing opening for filling of the reservoir per FIG. 3.
FIG. 8 is a figure similar to FIGS. 6 and 7 showing a piercing of a point of the soft cannula with the rigid hypodermic needle per FIG. 4.
FIG. 9 is a figure similar to FIGS. 6, 7, and 8 showing retraction of the rigid hypodermic needle per FIG. 5 and the resealing of the self-sealing element for delivery of drugs through the soft cannula.
FIG. 10 is a figure similar to FIG. 3 showing a pre-compressed needle-withdrawal spring activated by downward movement of the rigid hypodermic needle to remove the hypodermic needle after piercing the soft cannula.
FIG. 11 is one embodiment of a pump suitable for use with the reservoir system of the present invention.

Referring now to FIG. 6, in this regard, the T-housing 36 may have an upwardly facing opening that is accessible through a self-sealing elastomeric gland 50, for example, having a central opening 52 that naturally seals under the elasticity of the gland 50. Within the volume of the T-housing 36 past the elastomeric gland 50, the T-housing 36 provides a first passage downward into the hollow soft needle 38 and a second passage out of a side channel 54 to the tube 46. At this time a tip of the soft needle 38 is closed.

Referring now to FIG. 7, in an initial configuration as shown in FIG. 3, the rigid hypodermic needle 32 is received through the opening 52 of the gland 50 which seals around the hypodermic needle 32 to prevent liquid flow there past. The end of the hypodermic needle 32 is removed above the tip of the soft needle 38 providing a passageway for liquid expelled from the syringe 44 (per FIG. 3) out of the end of the hypodermic needle 32 and upward around the hypodermic needle 32 in the soft needle 38 into the T-housing 36 and out to the channel 54, through the tubing 46 into the reservoir 18. In this way the reservoir 18 may be filled with a standard syringe 44.

Referring now to FIGS. 4 and 8, after this filling operation, the syringe 44 may be removed, and outwardly extending trigger tabs 60 on either side of the Luer lock 30 (in the configuration of FIG. 3) may be pressed inward releasing a helical compression spring 62 pushing the Luer lock 30 and hypodermic needle 32 downward into the cannula assembly 34 to insert the soft needle 38 beneath the patient's skin. Further downward movement of the cannula assembly 34 is prevented by interference between the T-housing 36 and the foot 14 of the housing 16 causing the hypodermic needle 32 to break through the apex of the soft needle 38 opening the soft needle 38 to provide a passage of drug flow through the skin into the tissue of the patient 12.

Referring now to FIGS. 5 and 9, the Luer lock 30 and hypodermic needle 32 are then drawn upward, as will be discussed below, to be pulled out of the soft needle 38 (being fully removed from the T-housing 36 and the soft needle 38 which remains in the patient 14). The gland 50 closes to prevent leakage of fluid from the opening of the T-housing 36, and drug may now be delivered from the reservoir 18 through channel 54 down through the soft needle 38 through the open apex of the soft needle 38 into tissue of the patient 12. By removing the relatively stiff hypodermic needle 32 in favor of the soft needle 38, improved patient comfort may be obtained.

Referring to FIG. 10, a number of different mechanisms may be used to implement the needle insertion mechanism 24 to insert the hypodermic needle 32 and then remove it rapidly. In one embodiment, motion downward of the Luer lock 30 and hypodermic needle 32 is guided by the attached carriage mechanism 70 driven by the compression spring 62. The carriage mechanism 70 may be constrained to move along axis 40 without rotation and may also prevent rotation of the Luer lock 30 facilitating engagement and disengagement with the syringe 44. When the carriage mechanism 70 drops sufficiently low to have inserted the soft needle 38 and pierced its apex, the carriage mechanism 70 may strike and release wedge catches 72 holding in compression of a stronger compression spring 74 which then pushes the Luer lock 30, carriage mechanism 70, and hypodermic needle 32 upward. Other mechanisms including motor driven mechanisms or systems requiring manual operation by the patient may also be envisioned.

Referring now to FIGS. 2 and 11, a wide variety of different pumps may be employed to move liquid from the reservoir 18 including piezoelectric pumps, elastomeric bladders, and the like. In one embodiment, the reservoir 18 includes a piston pump 76 driven by the motor 20 to reciprocate a contained piston 78 inside a cylinder 80 provided within the cylinder 80 variable pumping volume. The tube 46 may be attached to a manifold 82 having a first one-way check valve 84 allowing material to flow upward through the tube 46 into the reservoir 18 during a charging of the reservoir per FIG. 7. A liquid blocking gas filter 81 allows the exit of gas from the reservoir 18 as this gas is displaced by the incoming medicine 85.

During pumping of the medicine to the patient per FIG. 5, the piston 78 draws liquid into the cylinder 80 through one-way inward facing check valve 86 and expels it through opposite facing one-way outward check valve 88 into the manifold and thus back down into the tube 46. Operation of this pump may be controlled by electronics as is generally understood in the art to manage controlled volumes and flow rates guided by sensors such as occlusion sensors pressure sensors and the like.

Certain terminology is used herein for purposes of reference only, and thus is not intended to be limiting. For example, terms such as "upper", "lower", "above", and "below" refer to directions in the drawings to which reference is made. Terms such as "front", "back", "rear", "bottom" and "side", describe the orientation of portions of the component within a consistent but arbitrary frame of reference which is made clear by reference to the text and the associated drawings describing the component under discussion. Such terminology may include the words specifically mentioned above, derivatives thereof, and words of similar import. Similarly, the terms "first", "second" and other such numerical terms referring to structures do not imply a sequence or order unless clearly indicated by the context.

When introducing elements or features of the present disclosure and the exemplary embodiments, the articles "a", "an", "the" and "said" are intended to mean that there are one or more of such elements or features. The terms "comprising", "including" and "having" are intended to be inclusive and mean that there may be additional elements or features other than those specifically noted. It is further to be understood that the method steps, processes, and operations described herein are not to be construed as necessarily requiring their performance in the particular order discussed or illustrated, unless specifically identified as an order of performance. It is also to be understood that additional or alternative steps may be employed.

References to "a microprocessor" and "a processor" or "the microprocessor" and "the processor," can be understood to include one or more microprocessors that can communicate in a stand-alone and/or a distributed environment(s), and can thus be configured to communicate via wired or wireless communications with other processors, where such one or more processor can be configured to operate on one or more processor-controlled devices that can be similar or different devices. Furthermore, references to memory, unless otherwise specified, can include one or more processor-readable and accessible memory elements and/or components that can be internal to the processor-controlled device, external to the processor-controlled device, and can be accessed via a wired or wireless network.

It is specifically intended that the present invention not be limited to the embodiments and illustrations contained herein and the claims should be understood to include modified forms of those embodiments including portions of the embodiments and combinations of elements of different embodiments as come within the scope of the following claims. All of the publications described herein, including patents and non-patent publications, are hereby incorporated herein by reference in their entireties.

To aid the Patent Office and any readers of any patent issued on this application in interpreting the claims appended hereto, applicants wish to note that they do not intend any of the appended claims or claim elements to invoke 35 U.S.C. 112(f) unless the words "means for" or "step for" are explicitly used in the particular claim.

What we claim is:

1. A transcutaneous drug delivery system, comprising:
a housing attachable to skin of a patient;
a syringe coupling supported by and exposed on an exterior of the housing providing a leak-free connection between a syringe and the syringe coupling; and
a hypodermic needle supported by the housing at a first end of the hypodermic needle to fluidly communicate with the syringe coupling to receive a liquid from the syringe when the syringe is coupled to the syringe coupling;
a reservoir to receive the liquid; and
a cannula assembly including:
a first opening to receive a second end of the hypodermic needle,
a second opening coupled to the reservoir, and a passage to a soft needle configured to deliver the liquid to the patient.

2. The transcutaneous drug delivery system of claim 1 further comprising a collar surrounding the syringe coupling on an exterior of the housing.

3. The transcutaneous drug delivery system of claim 2 wherein the collar extends outwardly from the housing by at least 1 cm.

4. The transcutaneous drug delivery system of claim 1 wherein the syringe coupling is a Luer-Lock connector providing a one way valve.

5. The transcutaneous drug delivery system of claim 1, wherein the syringe includes a Luer-Lock tip.

6. The transcutaneous drug delivery system of claim 1 wherein the soft needle is configured to receive the hypodermic needle therein.

7. The transcutaneous drug delivery system of claim 1 further comprising a first one way check valve permitting movement of the liquid from the cannula assembly to the reservoir and a second one way check valve permitting movement of the liquid from the reservoir to the cannula assembly.

8. The transcutaneous drug delivery system of claim 1 wherein an apex of the soft needle is pierceable by the hypodermic needle permitting passage of the hypodermic needle through the skin of the patient.

9. The transcutaneous drug delivery system of claim 1 further comprising a pump configured to draw liquid from the reservoir.

10. The transcutaneous drug delivery system of claim 9 wherein the pump comprises a motor configured to reciprocate a piston within a cylinder.

11. The transcutaneous drug delivery system of claim 1 further comprising a first compression spring configured to move the hypodermic needle along an insertion path through the skin of the patient in a released state.

12. The transcutaneous drug delivery system of claim 11 further comprising a second compression spring exerting a greater force than the first compression spring configured to move the hypodermic needle out of the skin of the patient.

13. The transcutaneous drug delivery system of claim 12 further comprising a spring catch retaining the second compression spring in a compressed state until the hypodermic needle is moved along the insertion path through the skin of the patient.

14. The transcutaneous drug delivery system of claim 1 further comprising an elastomeric gland covering the first opening of the cannula assembly and allowing the hypodermic needle to pierce the elastomeric gland and reseal when the hypodermic needle is removed from the elastomeric gland.

15. A method of transcutaneous delivery of a drug comprising the steps of:
attaching the housing of the transcutaneous drug delivery system of claim 1 to skin of a patient;
connecting a syringe to the syringe coupling;
inserting the second end of the hypodermic needle through the first opening;
expelling the drug from the syringe through the hypodermic needle and through the second opening to fill the reservoir; and
providing a fluid flow path from the reservoir through the second opening and through the passage to the soft needle to deliver the drug to the patient.

16. The method of claim 15 further comprising piercing an apex of the soft needle contemporaneously with piercing the skin of the patient with the hypodermic needle.

17. A transcutaneous drug delivery system, comprising:

a housing attachable to skin of a patient;

a syringe coupling supported by the housing providing a leak-free connection between a syringe and the syringe coupling;

a carriage mechanism configured to slidably move along an insertion path;

a hypodermic needle supported by the carriage mechanism at a first end of the hypodermic needle to fluidly communicate with the syringe coupling to receive a liquid from the syringe when the syringe is coupled to the syringe coupling;

a reservoir to receive the liquid from the hypodermic needle prior to inserting the hypodermic needle through the skin of the patient;

a first compression spring configured to move the carriage mechanism and the hypodermic needle along the insertion path to cause the hypodermic needle to pierce through the skin of the patient;

a second compression spring exerting a greater force than the first compression spring to move the hypodermic needle along the insertion path out of the skin of the patient; and a set of catches holding the second compression spring in a compressed state, wherein the set of catches are released by the carriage mechanism when the carriage mechanism is moved along the insertion path by the first compression spring.

18. The transcutaneous drug delivery system of claim 17 further comprising tabs configured to release the first compression spring.

\*　\*　\*　\*　\*